United States Patent [19]

Scholz et al.

[11] Patent Number: 6,040,336
[45] Date of Patent: Mar. 21, 2000

[54] PROSTANE DERIVATIVES AND THE COMBINATION THEREOF WITH ANTIBIOTICS IN THE TREATMENT OF BACTERIAL INFECTIONS

[75] Inventors: Peter Scholz; Jörg Weber; Klemens Angstwurm, all of Berlin, Germany

[73] Assignee: Schering Aktiengesellschaft, Berlin, Germany

[21] Appl. No.: 09/011,457

[22] PCT Filed: Aug. 6, 1996

[86] PCT No.: PCT/EP96/03481

§ 371 Date: Apr. 23, 1998

§ 102(e) Date: Apr. 23, 1998

[87] PCT Pub. No.: WO97/06806

PCT Pub. Date: Feb. 27, 1997

[30] Foreign Application Priority Data

Aug. 11, 1995 [DE] Germany .................... 195 30 884

[51] Int. Cl.[7] .................... A61K 31/34; A61K 31/21; A61K 31/19
[52] U.S. Cl. .................... 514/468; 514/510; 514/557; 514/898
[58] Field of Search .................... 514/468, 510, 514/557, 898

[56] References Cited

FOREIGN PATENT DOCUMENTS 011591  5/1980  European Pat. Off. .
084856  8/1983  European Pat. Off. .

*Primary Examiner*—Kimberly Jordan
*Attorney, Agent, or Firm*—Millen, White, Zelano & Branigan

[57] ABSTRACT

A method is described for treating bacterially induced meningitis, comprising administering a prostane derivative of formula I or Ia

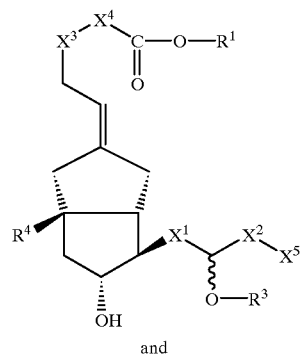

formula I

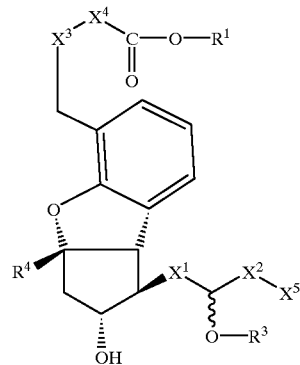

formula Ia wherein $X^1$, $X^2$, $X^3$, $X^4$, $X^5$, $R^1$, $R^2$, $R^3$ and $R^4$ are as described below, and the —O—$R^3$— group is in the α- or β-configuration. The prostane derivative can optionally comprise or serve as an adjuvant, and it can be administered in combination with an antiobiotic.

18 Claims, No Drawings

PROSTANE DERIVATIVES AND THE COMBINATION THEREOF WITH ANTIBIOTICS IN THE TREATMENT OF BACTERIAL INFECTIONS

This application is a 371 of PCT/EP96/03481, filed Aug. 6, 1996.

The invention relates to the use of prostane derivatives in the preparation of a medicament for the treatment of bacterially induced meningitis and also to the combination of prostane derivatives with antibiotics.

Despite great advances in antimicrobial therapy, mortality in the case of bacterial meningitis is high (M. N. SCHWARTZ (1984) Bacterial meningitis: more involved than just the meningitis. N. Engl. J. Med., 311: 912–914).

Pneumococci are aetiologically the most frequent causes of meningitis in adults and result in death in from 25% to 30% of cases. Clinical observations would suggest that an increase in the intracranial pressure (ICP), the formation of cerebral oedemas and cerebral vasculitis determine the fatal course of the meningitis (H.-W. PFISTER (1989): Complicated purulent meningitis of the adult: persisting high mortality caused by vasculitis and increased intracranial pressure, Nervenarzt, 60: 249–254). The inflammatory changes in bacterial meningitis are mediated by cytokines such as TNF. TNF can be detected in humans with pneumococcal meningitis. (K. J. TRACEY (1994) Tumor necrosis factor—alpha: In: The cytokine handbook A. THOMSON, eds. Academic Press London, pp. 289–304, and also: T. P. LEIST et al. (1988) Tumor necrosis factor alpha in cerebrospinal fluid during bacterial, but not viral, meningitis. Evaluation in murine model infections and in patients. J. Exp. Med., 167 (5): 1743–1748). CSF pleocytosis and cerebral oedema occur after the intracisternal increase in TNF (K. SAUKKOMEN et al. (1990) The role of cytokines in the generation of inflammation and tissue damage in experimental gram positive meningitis. J. Exp. Med. 171 (2): 439–448). That points to a transmigration of leucocytes and a breakdown of the blood/brain barrier.

EP 0 011 591 describes prostane derivatives and their preparation. Those prostane derivatives are compounds that are derived from prostacyclin ($PGI_2$). They contain a methylene group instead of the 9-ether-oxygen atom in the prostacyclin. Prostane derivatives are used in the treatment of various diseases, the cardiovascular and thrombo-aggregation-inhibiting action being especially important.

The use of prostane derivatives as medicaments is known from EP 0 011 591. That Application describes the lowering of peripheral, arterial and coronary vascular resistance, the inhibition of thrombocyte aggregation and breaking down of platelet thrombi, myocardial cytoprotection and therewith a lowering of the systemic blood pressure without at the same time reducing cardiac output and coronary blood supply; treatment of stroke, prophylaxis and treatment of coronary heart diseases, coronary thrombosis, cardiac infarction, peripheral arterial diseases, arteriosclerosis and thrombosis, treatment of shock, inhibition of broncho-constriction, inhibition of gastric acid secretion and cytoprotection of the gastric mucous membrane and intestinal mucous membrane; anti-allergic properties, lowering of pulmonary, vascular resistance and of pulmonary blood pressure, promotion of renal blood flow, use instead of heparin or as an adjuvant in haemofiltration dialysis, storage of blood plasma stocks, especially of blood platelet stocks, inhibition of labour pains, treatment of toxaemia of pregnancy, anti-proliferative action and increase of cerebral blood flow.

EP 0 055 208, EP 0 099 538 and EP 0 119 949 describe carbacyclin derivatives that have similar indications to those of the above-mentioned prostane derivatives.

EP 0 084 856 describes further prostane derivatives which have been proposed for use in inhibiting thrombocyte aggregation, in lowering the systemic blood pressure or in the treatment of gastric ulcers, with beraprost being given special mention.

The use of prostane derivatives in the treatment of immune responses is described in various publications. For example, the treatment of anti-allergic properties is mentioned, inter alia, in EP 0 011 591.

EP 0 055 208 describes, inter alia the anti-allergic action of carbacyclin derivatives.

The publication by H. J. GRUNDMANN et al. (1992) J. Infect. Dis. 165: 1–5) describes in detail the use of a prostane derivative, that is to say iloprost, in the treatment of septic shock.

DE 41 04 607 mentions the treatment of AIDS and diabetes with the aid of prostane derivatives.

The publication by K. SLIWA et al. (1991) Infection and Immunity, 59: 3846–3848) relates to the treatment of cerebral malaria with iloprost.

The object of the present invention is to use prostane derivatives for a further indication, and also to combine prostane derivatives with antibiotics.

It has, surprisingly, been found that prostane derivatives of the general formulae I and Ia

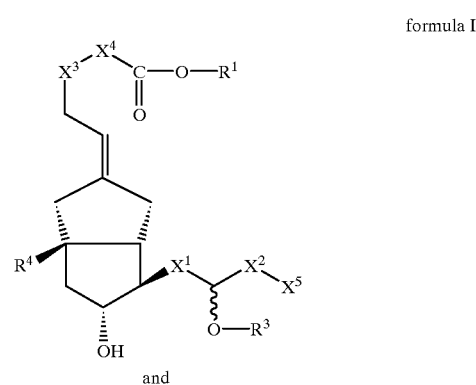

formula I and

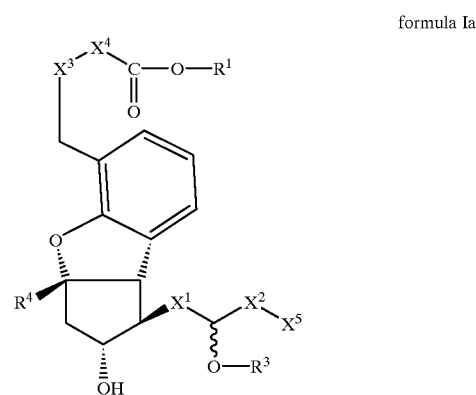

formula Ia wherein
$X^1$ is a —$CH_2$—$CH_2$—, trans —CH=CH— or a —C≡C— group,
$X^2$ is a linear or branched saturated hydrocarbon chain having from 1 to 6 carbon atoms,
$X^3$ is an —O— or —$CH_2$— group,
$X^4$ is a —$CH_2$— or —$(CH_2)_3$— group,
$X^5$ is a hydrogen atom or a —C≡C—$R^2$ group,
$R^1$ is a hydrogen atom, an alkyl group having from 1 to 6 carbon atoms, a cycloalkyl group having 5 or 6 carbon atoms or a phenyl group, R² is a linear or branched, saturated or unsaturated hydrocarbon chain having from 1 to 6 carbon atoms,
R³ is a hydrogen atom, an acyl radical having from 1 to 4 carbon atoms or a benzyl radical, and
R⁴ is a hydrogen atom or a methyl group;
the —O—R³— group being in the α- or β-configuration, and also salts thereof with physiologically tolerable bases when R¹ represents a hydrogen atom, can be used (for the preparation of a medicament) for the optional adjuvant treatment of bacterially induced meningitis.

Preference is given to the use according to the invention of the above-mentioned prostane derivatives of the general formula I wherein
X¹ is a trans —CH═CH— group,
X² is a linear or branched saturated hydrocarbon chain having from 2 to 4 carbon atoms,
X³ is a —CH₂— group,
X⁴ is a —CH₂— group,
X⁵ is a —C≡C—R² group,
R¹ is a hydrogen atom, an alkyl group having from 1 to 3 carbon atoms or a phenyl group,
R² is a linear or branched, saturated or unsaturated hydrocarbon chain having from 1 to 3 carbon atoms,
R³ is a hydrogen atom or an acyl radical having 2 carbon atoms, and
R⁴ is a hydrogen atom;
the —O—R³— group being in the α- or β-configuration, and their salts with physiologically tolerable bases when R¹ represents a hydrogen atom, (in the preparation of a medicament) for the optional adjuvant treatment of bacterially induced meningitis.

Especially preferred is the use according to the invention of the above-mentioned prostane derivatives of the general formula I wherein
X¹ is a trans —CH═CH— group,
X² is a methylethylene group, the methyl group being bonded to the first carbon atom of the ethylene group and the first carbon atom of the ethylene group facing the radical R¹,
X³ is a —CH₂— group,
X⁴ is a —CH₂— group,
X⁵ is a —C≡C—R² group,
R¹ is a hydrogen atom or a methyl group,
R² is a methyl group or an ethyl group,
R³ is a hydrogen atom or a formyl group, and
R⁴ is a hydrogen atom,
the —O—R³— group being in the α- or β-configuration, and their salts with physiologically tolerable bases when R¹ represents a hydrogen atom, (in the preparation of a medicament) for the optional adjuvant treatment of bacterially induced meningitis.

Especially preferred is the use according to the invention of an above-mentioned prostane derivative of the general formula I wherein
X¹ is a trans —CH═CH— group,
X² is a methylethylene group, the methyl group being bonded to the first carbon atom of the ethylene group and the first carbon atom of the ethylene group facing the radical R¹,
X³ is a —CH₂— group,
X⁴ is a —CH₂— group,
X⁵ is a —C≡C—R² group,
R¹ is a hydrogen atom,
R² is a methyl group,
R³ is a hydrogen atom, and
R⁴ is a hydrogen atom,
the —OH group being in the α- or β-configuration, and its salts with physiologically tolerable bases, (in the preparation of a medicament) for the optional adjuvant treatment of bacterially induced meningitis.

That compound has the name "iloprost" and has the systematic nomenclature 5-(E)-(1S,5S,6R)-7-hydroxy-6 [(E)-(3S,4RS)-3-hydroxy-4-methyl-1-octen-6-ynyl]bicyclo [3.3.0]octen-3-ylidene-pentanoic acid. That is the most preferred compound of the present invention.

A linear or branched saturated hydrocarbon chain having from 1 to 6 carbon atoms is understood to be, for example, methylene, ethylene, propylene or isopropylene, the methyl group being bonded to the first or second carbon atom of the ethylene, counting from the radical R¹; butylene, methylpropylene, ethylethylene or dimethylethylene, the methyl groups or ethyl groups being bonded at any point on the alkylene chain; pentyl, methylbutylene, dimethylpropylene, ethylpropylene or methylethyl-ethylene, the methyl groups or ethyl groups being bonded at any point on the alkylene chain; hexylene, methylpentylene, dimethylbutylene or methylethylpropylene, the methyl group or ethyl group being bonded at any point on the alkylene chain.

The alkyl group R¹ includes straight-chained or branched alkyl groups having from 1 to 6 carbon atoms, such as, for example, methyl, ethyl, propyl, butyl, isobutyl, tert-butyl, pentyl, neopentyl and hexyl.

The cycloalkyl group R¹ may contain 5 or 6 carbon atoms in the ring.

The alkyl group R² may consist of a linear or branched, saturated or unsaturated hydrocarbon chain having from 1 to 6 carbon atoms. Special mention may be made of the methyl, ethyl, propyl, butyl, isobutyl, tert-butyl, pentyl, hexyl, butenyl, isobutenyl, propenyl, pentenyl and hexenyl groups.

The acyl group R³ may consist of a straight-chained or branched-chain acyl group having from 1 to 4 carbon atoms, such as, for example, acetyl, propionyl, butyryl and isobutyryl.

Suitable for salt-formation with the free acids are inorganic and organic bases such as are known to the person skilled in the art for the formation of physiologically tolerable salts. There may be mentioned by way of example: alkali metal hydroxides, such as sodium and potassium hydroxide, alkaline earth metal hydroxides, such as calcium hydroxide, ammonia, amines, such as ethanolamine, diethanolamine, triethanolamine, N-methylglucamine, morpholine, tris(hydroxymethyl)methylamine etc. The β-cyclodextrin clathrate formation is carried out as described in EP 0 259 468. All subject matter mentioned in that patent application is included by reference in the present application.

Surprisingly, prostane derivatives are suitable for the treatment of encephalitis in bacterial meningitis which occurs as a result of bacterial components after the bacteria have been destroyed by treatment with antibiotics. Hitherto, antibiotics (for example penicillins) in combination with glucocorticoids (dexamethasone) were used for the treatment (E. TUOMANEN (1993) Bakterielle Meningitis und die Blut - Hirn - Schranke, Spektrum der Wissenschaft, 4: 86–90).

The present invention also relates to the use of the preferred compounds cicaprost, eptaloprost, ciprosten and/or beraprost and their salts in the treatment of bacterially induced meningitis. The compounds including iloprost are listed in Table I with reference to their structure.

The present invention also relates to the use according to the invention of prostane derivatives together with physiologically tolerable pharmacological excipients and carriers. Such substances are described in Remington's Pharmaceutical Science, 15th ed. Mack Publishing Company, Easton Pa. (1989).

The methods of preparation for a number of the prostane derivatives that can be used according to the invention are described in detail in EP 0 011 591 or EP 0 084 856. The compounds of the general formulae I and Ia that are not expressly mentioned therein do not, however, differ in terms of the method of preparation. Their preparation lies within the general knowledge of a person skilled in the art.

The invention relates also to a combination of (i) prostane derivatives with (ii) antibiotics. In that case, the prostane derivatives and the antibiotics may be administered at the same time or at different times by means of the same or different modes of administration. Modes of administration are especially enteral, preferably oral, most preferably parenteral. Suppositories, tablets, capsules, drops, injection solutions and suspensions are the appropriate forms for administration.

A combination of (i) prostane derivatives and (ii) antibiotics is preferred as a therapeutic agent. In that case, the prostane derivatives and the antibiotics may be administered at the same time or at different times by means of the same or different modes of administration.

Especially preferred is the use of a combination of (i) prostane derivatives and (ii) antibiotics in the treatment of bacterially induced meningitis. In that case, the prostane derivatives and the antibiotics may be administered at the same time or at different times by means of the same or different modes of administration.

Antibiotics, their action and use are described in detail in Römpp Chemie-Lexikon, Jürgen FALBE and Manfred REGITZ (eds.), ninth edition, Stuttgart 1989, ISBN 3-13-734609-6, pages 206 to 208. The antibiotics described therein can be used in combination with the prostane derivatives of the general formulae I and Ia.

In the present study, changes in the regional cerebral blood flow (rCBF), the intracranial pressure (ICP), cerebral oedema formation and in the number of cells in the cerebral fluid (CSF) are measured during the early phase of pneumococcus-induced meningitis in rats. Those parameters for encephalitis and destruction of the blood/brain barrier are increased after intracisternal injection of pneumococci in rats. They can be reduced in the presence of the prostane derivatives according to the invention.

The prostane derivatives that can be used according to the invention demonstrate the action in the above-mentioned test at concentrations of from 1 to 500 ng per kg body weight and per minute.

The above-mentioned in vivo test system simulates the increased inflammation reaction resulting from antibiotic bacteriolysis and is therefore highly suitable for experimental testing of adjuvant strategy therapies (H. W. PFISTER et al. (1992) Antioxidants attenuate microvascular changes in the early phase of experimental pneumococcal meningitis in rats. Stroke, 23 (12): 1798–1804).

The compounds of the general formulae I and Ia are suitable for the optional adjuvant treatment of bacterially induced meningitis. A combination of compounds of the general formula I or Ia and of antibiotics is preferred. A combination of compounds of the general formula I or Ia and antibiotics as a therapeutic agent is advantageous. Also preferred is a use of a combination of compounds of the general formula I or Ia and of antibiotics in the treatment of bacterially induced meningitis.

For that therapeutic action, the suitable dose varies and depends, for example, on the compound of the general formulae I and Ia used, on the host, the mode of administration and the type and severity of the conditions that are to be treated. Generally, however, satisfactory results in animals are to be expected at daily doses of from 1 to 30 µg/kg body weight. In larger mammals, for example humans, a recommended dose is from 0.1 to 3 mg of the prostane derivatives of the general formulae I and Ia. Preferred values are from 0.3 to 1 mg per day, the administration generally lasting for to up to 4 days. The daily dose of prostane derivatives may be administered advantageously in from 2 to 4 part doses per day. An antibiotic may be administered therewith.

The prostane derivatives of the general formulae I and Ia may be administered in the case of systemic treatment by any customary route, especially enterally, preferably orally, most preferably parenterally. Suppositories, tablets, capsules, drops, injection solutions or suspensions are the appropriate forms for administration.

The prostane derivative iloprost is the especially preferred compound. It is administered, for example in larger mammals, for example humans, in the above-mentioned manner. The doses are in that case smaller than those indicated above by a factor of 2. An infusion solution in the form of a longer-term infusion preparation in a customary aqueous solvent, for example physiological saline solution, is the preferred form of administration for systemic treatment. In that case, from 0.1 ng/kg/min to 100 ng/kg/min, preferably from 1 to 10 ng/kg/min, are administered.

Therapeutic compositions can also be used that comprise a prostane derivative of the general formula I or Ia together with at least one pharmaceutical carrier, additive or diluent, all of which are physiologically tolerable. Such compositions can be prepared in a manner known per se. Pharmacologically tolerable and suitable excipients and carriers are described, for example, in Remington's Pharmaceutical Science, 15th ed. Mack Publishing Company, Easton Pa. (1980). The use of cyclodextrin clathrates, which are described in European Patent Specification EP 0 259 468, is also possible.

EXAMPLE

Meningitis is induced in anaesthetized adult male Wistar rats (from 250 to 350 g) by intracisternal injection of 75 µl containing the equivalent of $1 \times 10^7$ cfu (colony forming units) of pneumococcal cell wall components. In the control animals, 75 µl of physiological saline solution is injected into the cisterna magna (T. P. LEIST (1988) Tumor necrosis factor alpha in cerebrospinal fluid during bacterial, but not viral, meningitis. Evaluation in murine model infections and in patients. J. Exp. Med. 167 (5): 1743–1748). In the third group, in addition to the intracisternal injection of pneumococci, iloprost is administered i.v. in a dose of 1 µg/h/kg.

The regional cerebral blood flow and the intracranial pressure are determined 2, 4 and 6 hours after the intracranial injection of pneumococci and the technical procedure is described precisely in the following publications: H.-W. PFISTER et al. (1990) J. Cerebral Blood Flow and Metabolism, 10: 914–922, and also H.-W. PFISTER et al. (1992) Stroke, 23 (12): 1798–1804.

The percentage content of cerebral fluid and the number of cells per µl of CSF are measured 6 hours after the injection of pneumococci, as described in H.-W. PFISTER et al. (1990) J. Cerebral Blood Flow and Metabolism, 10: 914–922.

As can be seen from Tables 1 to 4, the prostane derivatives used according to the invention reduce significantly the pneumococcus-induced increase in cerebral blood flow, the intracranial blood pressure, the percentage proportion of cerebral fluid and the number of cells per µl of CSF. The data are studied for significant differences with the aid of the Student-Newman-Keuls test (statistic package: SPSS for MS Windows Release 6.1; Oneway, Analysis of Variance, significance level 0.05).

TABLE I

| Group/parameter | LDF 0h | LDF 2h | LDF 4h | LDF 6h |
|---|---|---|---|---|
| 1. Control n = 8 | 100 | 102 ± 5 | 108 ± 9 | 114 ± 11 |
| 2. PCW n = 8 | 100 | 150 ± 30 | 208 ± 40 | 252 ± 48 |
| 3. Iloprost i.v. n = 5 | 100 | 113 ± 3 | 130 ± 17 | 147 ± 19 |

TABLE 2

| Group/parameter | ICP 0h | ICP 2h | ICP 4h | ICP 6h |
|---|---|---|---|---|
| 1. Control n = 8 | 3.2 ± 1.7 | 3.9 ± 1.5 | 3.9 ± 1.6 | 3.6 ± 1.4 |
| 2. PCW n = 8 | 3.9 ± 1.5 | 6.3 ± 2.2 | 8.9 ± 3.5 | 10.9 ± 3.6 |
| 3. Iloprost i.v. n = 4 | 3.2 ± 1.3 | 4.2 ± 1.8 | 4.2 ± 1.2 | 4.6 ± 1.1 |

TABLE 3

| Group/parameter | Cells/µl CSF 0h | Cells/µl CSF 6h |
|---|---|---|
| 1. Control n = 8 | 4 ± 3 | 6 ± 6 |
| 2. PCW n = 7/6 | 5 ± 3 | 2287 ± 978 |
| 3. Iloprost i.v. n = 5 | 4 ± 3 | 518 ± 190 |

TABLE 4

| Group/parameter | Cerebral fluid in % |
|---|---|
| 1. Control n = 8 | 78.50 ± 0.55 |
| 2. PCW n = 8 | 79.89 ± 0.51 |
| 3. Iloprost i.v. n = 5 | 78.55 ± 0.15 |

Legend:

LDF=Laser/Doppler/Flow (regional cerebral blood flow)
ICP=intracranial pressure
PCW=pneumococcal cell wall components
aa) Control: NaCl i.c.
bb) PCW: PCW i.c. equivalent of $1 \times 10^7$ CFU Strept. pneum.—untreated meningitis.
cc) Iloprost i.v.: PCW i.c. and iloprost continuously i.v. 1 µg/h/kg
Blood gases, mean pressure of final expiratory $CO_2$ within the normal range;
Anaesthesia: pentobarbital 100 mg/kg.

What is claimed is:

1. A method for treating bacterially induced meningitis, comprising administering an effective amount of a compound of formula I or Ia

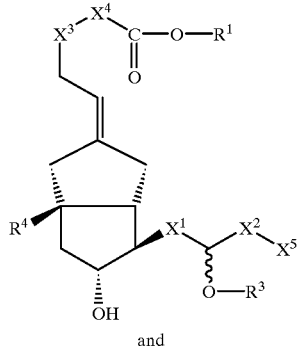

formula I

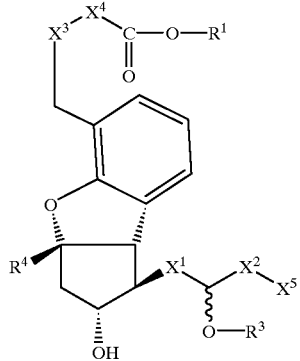

formula Ia wherein
$X^1$ is a —$CH_2$—$CH_2$—, trans —CH=CH— or —C≡C— group,
$X^2$ is a linear or branched saturated hydrocarbon chain having from 1 to 6 carbon atoms,
$X^3$ is an —O— or —$CH_2$— group,
$X^4$ is a —$CH_2$— or (—$CH_2$)$_3$— group,
$X^5$ is a hydrogen atom or a —C≡C—$R^2$ group,
$R^1$ is a hydrogen atom, an alkyl group having from 1 to 6 carbon atoms, a cycloalkyl group having 5 or 6 carbon atoms or a phenyl group,
$R^2$ is a linear or branched, saturated or unsaturated hydrocarbon chain having from 1 to 6 carbon atoms,
$R^3$ is a hydrogen atom, an acyl radical having from 1 to 4 carbon atoms or a benzyl radical, and
$R^4$ is a hydrogen atom or a methyl group,
wherein the O—$R^3$— group is in the α- or β-configuration,
or a salt thereof with a physiologically tolerable base when $R^1$ represents a hydrogen atom.

2. The method according to claim 1, wherein
$X^1$ is a trans —CH=CH— group,
$X^2$ is a linear or branched saturated hydrocarbon chain having from 2 to 4 carbon atoms,
$X^3$ is a —$CH_2$— group,
$X^4$ is a —$CH_2$— group,
$X^5$ is a —C≡C—$R^2$ group,
$R^1$ is a hydrogen atom, an alkyl group having from 1 to 3 carbon atoms or a phenyl group,
$R^2$ is a linear or branched, saturated or unsaturated hydrocarbon chain having from 1 to 3 carbon atoms,
$R^3$ is a hydrogen atom or an acyl radical having from 2 carbon atoms, and $R^4$ is a hydrogen atom.

3. The method according to claim 2, wherein
$X^1$ is a trans —CH═CH— group,
$X^2$ is a methylethylene group, wherein the methyl group is bonded to the first carbon atom of the ethylene group and the first carbon atom of the ethylene group facing the radical $R^1$,
$X^3$ is a —CH$_2$— group,
$X^4$ is a —CH$_2$— group,
$X^5$ is a —C≡C—$R^2$ group,
$R^1$ is a hydrogen atom or a methyl group,
$R^2$ is a methyl group or an ethyl group,
$R^3$ is a hydrogen atom or a formyl group, and
$R^4$ is a hydrogen atom.

4. The method according to claim 3, wherein
$X^1$ is a trans —CH═CH— group,
$X^2$ is a methylethylene group, wherein the methyl group is bonded to the first carbon atom of the ethylene group and the first carbon atom of the ethylene group facing the radical $R^1$,
$X^3$ is a —CH$_2$— group,
$X^4$ is a —CH$_2$— group,
$X^5$ is a —C≡C—$R^2$ group,
$R^1$ is a hydrogen atom,
$R^2$ is a methyl group,
$R^3$ is a hydrogen atom, and
$R^4$ is a hydrogen atom.

5. The method of claim 4, further comprising administering an antibiotic.

6. The method of claim 4, wherein said compound is administered enterally, orally or parenterally.

7. The method according to claim 1, wherein said compound is cicaprost, eptaloprost, ciprosten and/or beraprost or a salt thereof.

8. The method according to claim 1, further comprising administering a physiologically tolerable pharmacological excipient and/or carrier.

9. The method of claim 1, further comprising administering antibiotic.

10. The method of claim 9, wherein said compound and said antibiotic are administered at the same time.

11. The method of claim 9, wherein said compound and said antibiotic are administered at different times.

12. The method of claim 11, wherein said compound is administered in a dose of from 1 to 10 ng/kg/min.

13. The method of claim 9, wherein said compound and/or said antibiotic are administered enterally, orally or parenterally.

14. The method of claim 1, wherein said acyl group of $R^3$ is a straight-chained or branched-chain acyl group having from 1 to 4 carbon atoms.

15. The method of claim 1, wherein said acyl group of $R^3$ is acetyl, propionyl, butyryl or isobutyryl.

16. The method of claim 1, wherein the allyl group $R^2$ is methyl, ethyl, propyl, butyl, isobutyl, tert-butyl, pentyl, hexyl, butenyl, isobutenyl, propenyl, pentenyl or hexenyl.

17. The method of claim 1, wherein said compound is administered in a dose of from 0.3 to 1 mg per day.

18. A method for treating bacterially induced meningitis, comprising administering an effective amount of a clathrate of a compound of formula I or Ia:

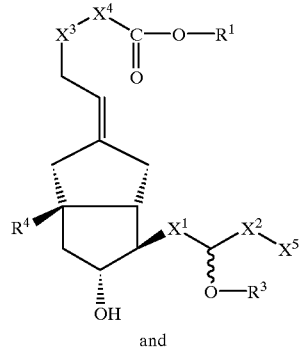

formula I and

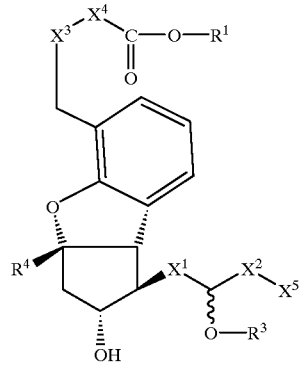

formula Ia wherein
$X^1$ is a —CH$_2$—CH$_2$—, trans —CH═CH— or —C≡C— group,
$X^2$ is a linear or branched saturated hydrocarbon chain having from 1 to 6 carbon atoms,
$X^3$ is an —O— or —CH$_2$— group,
$X^4$ is a —CH$_2$— or (—CH$_2$)$_3$— group,
$X^5$ is a hydrogen atom or a —C≡C—$R^2$ group,
$R^1$ is a hydrogen atom, an alkyl group having from 1 to 6 carbon atoms, a cycloalkyl group having 5 or 6 carbon atoms or a phenyl group,
$R^2$ is a linear or branched, saturated or unsaturated hydrocarbon chain having from 1 to 6 carbon atoms,
$R^3$ is a hydrogen atom, an acyl radical having 1 to 4 carbon atoms or a benzyl radical, and
$R^4$ is a hydrogen atom or a methyl group,
wherein the O—$R^3$— group is in the α- or β-configuration,
or a salt thereof with a physiologically tolerable base when $R^1$ represents a hydrogen atom.

* * * * *